United States Patent
Ferree

(10) Patent No.: US 6,969,404 B2
(45) Date of Patent: Nov. 29, 2005

(54) ANNULUS FIBROSIS AUGMENTATION METHODS AND APPARATUS

(76) Inventor: Bret A. Ferree, 1238 Cliff Laine Dr., Cincinnati, OH (US) 45208

(*) Notice: Subject to any disclaimer, the term of this patent is extended or adjusted under 35 U.S.C. 154(b) by 175 days.

(21) Appl. No.: 10/120,763

(22) Filed: Apr. 11, 2002

(65) Prior Publication Data

US 2002/0165542 A1   Nov. 7, 2002

Related U.S. Application Data

(63) Continuation-in-part of application No. 09/807,820, filed as application No. PCT/US00/14708 on May 30, 2000, now abandoned, and a continuation-in-part of application No. 09/690,536, filed on Oct. 16, 2000, now Pat. No. 6,371,990, and a continuation-in-part of application No. 09/638,241, filed on Aug. 14, 2000, and a continuation-in-part of application No. 09/639,309, filed on Aug. 14, 2000, now Pat. No. 6,419,702, which is a continuation-in-part of application No. 09/638,726, filed on Aug. 14, 2000, now Pat. No. 6,340,369, and a continuation-in-part of application No. 09/454,908, filed on Dec. 3, 1999, now Pat. No. 6,491,724, and a continuation-in-part of application No. 09/415,382, filed on Oct. 8, 1999, now Pat. No. 6,419,704.

(51) Int. Cl.$^7$ ............................................... A61F 2/44

(52) U.S. Cl. ................................................. 623/17.11

(58) Field of Search ....................... 606/53, 61, 76, 606/78, 99; 623/17.11, 17.12, 17.13, 17.15, 623/17.16, 23.52, 23.53, 23.54, 23.55, 23.61, 623/23.63, 23.67

(56) References Cited

U.S. PATENT DOCUMENTS 2,677,369 A    5/1954  Knowles ...................... 128/92

(Continued)

FOREIGN PATENT DOCUMENTS

WO    WO 97/27893    * 8/1997    .......... A61M 19/00

OTHER PUBLICATIONS

Steven Frick MD, SPINE vol. 19 No. 16 pp. 1826-1835, 1994.

(Continued)

*Primary Examiner*—Kevin Shaver
*Assistant Examiner*—David Comstock
(74) *Attorney, Agent, or Firm*—Gifford, Krass, Groh, Sprinkle, Anderson & Citkowski, PC

(57) ABSTRACT

A device and method are used in fortifying an intervertebral disc having an annulus fibrosis with an inner wall. According to the method, a hole is formed through the annulus fibrosis, and a collapsed bag is inserted into the disc through the hole. The bag is inflated, or allowed to expand within the disc space, then filling with one or more biocompatible materials. The hole in the annulus fibrosis is then closed. In one preferred embodiment, the bag includes an inflatable bladder or balloon which is filled with a gas or liquid to expand the bag. In an alternative preferred embodiment, the bag includes a self-expanding frame that assumes a collapsed state for introduction into the disc space and an expanded state once inserted through the hole in the annulus. The self-expanding frame is composed of a shape-memory material, for example. The bag preferably features a wall which is porous to allow for the diffusion of body fluids therethrough, and the bag and/or frame may be fastened to the inner wall of the annulus at one or more points. The biocompatible material may include autograft nucleus pulposis, allograft nucleus pulposis or xenograft nucleus pulposis. In the preferred embodiment, the biocompatible material includes morselized nucleus or annulus from the same disc.

47 Claims, 3 Drawing Sheets

U.S. PATENT DOCUMENTS

| | | | |
|---|---|---|---|
| 3,366,975 A | 2/1968 | Pangman | 3/36 |
| 3,426,364 A | 2/1969 | Lumb | 3/1 |
| 3,551,560 A | 12/1970 | Thiele | 424/95 |
| 3,593,342 A | 7/1971 | Neibauer | 3/1 |
| 3,648,294 A | 3/1972 | Shahrestani | 3/1 |
| 3,855,638 A | 12/1974 | Pilliar | 3/1 |
| 3,867,728 A | 2/1975 | Stubstad et al. | 3/1 |
| 3,878,595 A | 4/1975 | Froning | 3/1 |
| 3,883,902 A | 5/1975 | Lynch | 3/36 |
| 4,229,839 A | 10/1980 | Schwemmer | 3/1.91 |
| 4,309,777 A | 1/1982 | Patil | 3/1.91 |
| 4,349,921 A | 9/1982 | Kuntz | 3/1 |
| 4,413,359 A | 11/1983 | Akiyama et al. | 3/1 |
| 4,512,338 A | 4/1985 | Balko et al. | 128/1 R |
| 4,663,358 A | 5/1987 | Hyon et al. | 521/64 |
| 4,707,872 A | 11/1987 | Hessel | 5/451 |
| 4,714,469 A | 12/1987 | Kenna | 623/17 |
| 4,743,256 A | 5/1988 | Brantigan | 128/898 |
| 4,759,766 A | 7/1988 | Buettner-Janz et al. | 623/17 |
| 4,772,287 A | 9/1988 | Ray et al. | 623/17 |
| 4,801,299 A | 1/1989 | Brendel et al. | 623/16.11 |
| 4,834,757 A | 5/1989 | Brantigan | 623/17 |
| 4,863,477 A | 9/1989 | Monson | 623/17.11 |
| 4,874,389 A | 10/1989 | Downey | 623/17 |
| 4,904,260 A | 2/1990 | Ray et al. | 623/17 |
| 4,904,261 A | 2/1990 | Dove et al. | 623/17 |
| 4,911,718 A | 3/1990 | Lee et al. | 623/17 |
| 4,917,704 A | 4/1990 | Frey et al. | 623/17 |
| 4,932,969 A | 6/1990 | Frey et al. | 623/17 |
| 4,946,378 A | 8/1990 | Hirayama et al. | 623/17 |
| 5,002,576 A | 3/1991 | Furhmann et al. | 623/17 |
| 5,015,255 A | 5/1991 | Kuslich | 623/17 |
| 5,035,716 A | 7/1991 | Downey | 623/17 |
| 5,047,055 A | 9/1991 | Bao et al. | 623/17 |
| 5,059,193 A * | 10/1991 | Kuslich | 606/61 |
| 5,071,437 A | 12/1991 | Steffee | 623/17 |
| 5,100,422 A | 3/1992 | Berguer et al. | 606/151 |
| 5,108,438 A | 4/1992 | Stone | 623/17 |
| 5,123,926 A | 6/1992 | Pisharodi | 623/17 |
| 5,147,374 A | 9/1992 | Fernandez | 606/151 |
| 5,171,278 A | 12/1992 | Pishrodl | 623/17 |
| 5,171,280 A | 12/1992 | Baumgartner | 623/17 |
| 5,171,281 A | 12/1992 | Parsons et al. | 623/17 |
| 5,192,326 A | 3/1993 | Bao et al. | 623/17 |
| 5,246,458 A | 9/1993 | Graham | 623/17 |
| 5,258,031 A | 11/1993 | Salib et al. | 623/17 |
| 5,258,043 A | 11/1993 | Stone | 623/66 |
| 5,263,953 A | 11/1993 | Bagby | 606/61 |
| 5,304,194 A | 4/1994 | Chee et al. | 606/191 |
| 5,314,477 A | 5/1994 | Marnay | 623/17 |
| 5,320,644 A | 6/1994 | Baumgartner | 623/17 |
| 5,342,394 A | 8/1994 | Matsuno et al. | 606/213 |
| 5,370,660 A | 12/1994 | Weinstein et al. | 606/215 |
| 5,370,697 A | 12/1994 | Baumgartner | 623/17 |
| 5,375,823 A | 12/1994 | Navas | 267/195 |
| 5,390,683 A | 2/1995 | Pisharodi | 128/898 |
| 5,401,269 A | 3/1995 | Buttner-Janz et al. | 623/17 |
| 5,425,772 A | 6/1995 | Brantigan | 623/17 |
| 5,425,773 A | 6/1995 | Boyd et al. | 623/17 |
| 5,458,642 A | 10/1995 | Beer et al. | 623/17 |
| 5,464,439 A | 11/1995 | Gendler | 623/16.11 |
| 5,496,318 A | 3/1996 | Howland et al. | 606/53 |
| 5,514,180 A | 5/1996 | Heggeness et al. | 623/17.11 |
| 5,534,028 A | 7/1996 | Bao et al. | 623/17 |
| 5,534,030 A | 7/1996 | Navarro et al. | 623/17 |
| 5,540,715 A | 7/1996 | Katsaros et al. | 606/213 |
| 5,545,229 A | 8/1996 | Parsons et al. | 623/17 |
| 5,549,679 A * | 8/1996 | Kuslich | 623/17.12 |
| 5,554,191 A | 9/1996 | Lahille et al. | 623/17 |
| 5,556,431 A | 9/1996 | Buttner-Janz | 623/17 |
| 5,562,736 A | 10/1996 | Ray et al. | 623/17 |
| 5,571,189 A | 11/1996 | Kuslich | 623/17.12 |
| 5,609,635 A | 3/1997 | Michelson | 623/17 |
| 5,643,329 A | 7/1997 | Solomonow et al. | 607/43 |
| 5,645,596 A | 7/1997 | Kim et al. | 623/17 |
| 5,645,597 A | 7/1997 | Krapiva | 623/17 |
| 5,653,763 A | 8/1997 | Ericco et al. | 623/17 |
| 5,674,294 A | 10/1997 | Bainville et al. | 623/17 |
| 5,674,296 A | 10/1997 | Bryan et al. | 623/17 |
| 5,681,310 A | 10/1997 | Yuan et al. | 606/61 |
| 5,683,465 A | 11/1997 | Shinn et al. | 623/17 |
| 5,702,450 A | 12/1997 | Bisserie | 623/17 |
| 5,711,960 A | 1/1998 | Shikinami | 424/426 |
| 5,716,416 A | 2/1998 | Lin | 623/17 |
| 5,776,196 A | 7/1998 | Matsuzaki et al. | 623/17 |
| 5,782,919 A | 7/1998 | Zdeblick et al. | 623/17 |
| 5,800,549 A | 9/1998 | Bao et al. | 623/17 |
| 5,800,550 A | 9/1998 | Sertich | 623/17 |
| 5,824,093 A | 10/1998 | Ray et al. | 623/17 |
| 5,824,094 A | 10/1998 | Serhan et al. | 623/17 |
| 5,827,328 A | 10/1998 | Butterman | 623/17 |
| 5,865,845 A | 2/1999 | Thalgott | 623/17 |
| 5,865,846 A | 2/1999 | Bryan et al. | 623/17 |
| 5,865,847 A | 2/1999 | Kohrs et al. | 623/17 |
| 5,865,848 A | 2/1999 | Baker | 623/17.11 |
| 5,879,366 A | 3/1999 | Shaw et al. | 606/213 |
| 5,885,287 A | 3/1999 | Bagby | 606/61 |
| 5,888,226 A | 3/1999 | Rogozinski | 623/17 |
| 5,888,227 A | 3/1999 | Cottle | 623/17 |
| 5,893,889 A | 4/1999 | Harrington | 623/17 |
| 5,893,890 A | 4/1999 | Pisharodi | 623/17.11 |
| 5,895,427 A | 4/1999 | Kuslich et al. | 623/17 |
| 5,897,593 A | 4/1999 | Kohrs et al. | 623/17 |
| 5,899,941 A | 5/1999 | Nishijima et al. | 623/17 |
| 5,906,616 A | 5/1999 | Pavlov | 606/61 |
| 5,916,225 A | 6/1999 | Kugel | 606/151 |
| 5,928,284 A | 7/1999 | Mehdizadeh | 623/17 |
| 5,964,807 A | 10/1999 | Gan et al. | 623/17.11 |
| 5,976,174 A | 11/1999 | Ruiz | 606/213 |
| 5,976,186 A | 11/1999 | Bao et al. | 623/17 |
| 5,989,291 A | 11/1999 | Ralph et al. | 623/17.13 |
| 6,007,570 A | 12/1999 | Sharkey et al. | 606/15 |
| 6,019,793 A | 2/2000 | Perren et al. | 623/17.11 |
| 6,022,376 A | 2/2000 | Assell et al. | 623/17.16 |
| 6,024,754 A | 2/2000 | Engelson | 606/213 |
| 6,060,053 A | 5/2000 | Atala | 424/93.7 |
| 6,066,325 A | 5/2000 | Wallace et al. | 424/400 |
| 6,077,987 A | 6/2000 | Breitbart et al. | 623/11.11 |
| 6,090,112 A | 7/2000 | Zucherman et al. | 606/61 |
| 6,102,950 A | 8/2000 | Vaccaro | 623/17.11 |
| 6,110,210 A | 8/2000 | Norton et al. | 623/17.16 |
| 6,113,639 A | 9/2000 | Ray et al. | 623/17.16 |
| 6,117,174 A | 9/2000 | Nolan | 623/17.11 |
| 6,132,465 A | 10/2000 | Ray et al. | 623/17.16 |
| 6,143,032 A | 11/2000 | Schafer et al. | 623/17.11 |
| 6,146,420 A | 11/2000 | McKay | 623/17.11 |
| 6,183,518 B1 | 2/2001 | Ross et al. | 623/17.16 |
| 6,187,048 B1 | 2/2001 | Milner et al. | 623/17.12 |
| 6,190,414 B1 | 2/2001 | Young et al. | 623/17.15 |
| 6,193,757 B1 | 2/2001 | Foley et al. | 623/17.16 |
| 6,197,586 B1 | 3/2001 | Bhatnagar et al. | 435/395 |
| 6,206,922 B1 | 3/2001 | Zdeblick et al. | 623/17.11 |
| 6,221,109 B1 | 4/2001 | Geistlich et al. | 623/17.11 |
| 6,224,630 B1 | 5/2001 | Bao et al. | 623/17.16 |
| 6,231,615 B1 | 5/2001 | Preissman | 623/23.73 |
| 6,245,107 B1 | 6/2001 | Ferree | 623/17 |
| 6,245,108 B1 | 6/2001 | Biscup | 623/17.11 |
| 6,264,695 B1 * | 7/2001 | Stoy | 623/17.16 |
| 6,340,369 B1 | 1/2002 | Ferree | 623/17.11 |
| 6,352,557 B1 | 3/2002 | Ferree | 623/17.11 |
| 6,371,990 B1 | 4/2002 | Ferree | 623/17.16 |
| 6,419,702 B1 | 7/2002 | Ferree | 623/17.11 |

| | | | |
|---|---|---|---|
| 6,419,704 B1 | 7/2002 | Ferree | 623/17.12 |
| 6,425,919 B1 * | 7/2002 | Lambrecht | 623/17.16 |
| 6,482,235 B1 * | 11/2002 | Lambrecht et al. | 623/17.16 |
| 6,488,710 B2 * | 12/2002 | Besselink | 623/17.15 |
| 6,491,724 B1 | 12/2002 | Ferree | 623/17.11 |
| 2002/0077701 A1 * | 6/2002 | Kuslich | 623/17.12 |
| 2002/0147497 A1 * | 10/2002 | Belef et al. | 623/17.12 |
| 2003/0074075 A1 * | 4/2003 | Thomas et al. | 623/17.16 |

OTHER PUBLICATIONS

Orthopedics Today, Jul. 2000.
"Proceedings 14th Annual Meeting" North American Spine Society, Oct. 1999.
"Proceedings 13th annual Meeting" North American Spine Society, Oct. 1998.

* cited by examiner-

FLAP

FLAP

ANNULUS FIBROSIS AUGMENTATION METHODS AND APPARATUS

REFERENCE TO RELATED APPLICATIONS

This application is a continuation-in-part of U.S. patent application Ser. No. 09/807,820, filed Apr. 19, 2001, now abandoned, which is a 371 of PCT/US00/14708, filed May 30, 2000; and Ser. No. 09/638,241, filed Aug. 14, 2000; and Ser. No. 09/454,908, filed Dec. 3, 1999 now U.S. Pat. No. 6,491,724; and Ser. No. 09/639,309, filed Aug. 14, 2000 now U.S. Pat. No. 6,419,702; and Ser. No. 09/690,536, filed Oct. 16, 2000, now U.S. Pat. No. 6,371,990, which is a continuation-in-part of U.S. patent application Ser. No. 09/638,726, filed Aug. 14, 2000, now U.S. Pat. No. 6,340,369; and Ser. No. 09/415,382, filed Oct. 8, 1999, now U.S. Pat. No. 6,419,704 the entire contents of each application being incorporated herein by reference.

FIELD OF THE INVENTION

This invention relates generally to human spinal surgery and, in particular, to methods and apparatus for augmenting the annulus fibrosis while controlling vertebral motion, thereby preventing additional annular tears and attendant discomfort.

BACKGROUND OF THE INVENTION

According to human anatomy, spinal function is dependent upon the intervertebral disc and the facet joints. In a sense, the annulus fibrosis, nucleus pulpous, and the facet joints form the legs of a three-legged stool.

To restore disc height resulting, for example, from degenerative disease, prosthetic discs are used to replace only the nucleus pulpous. Reference is made to my co-pending patent application Ser. No. 09/415,382, which discusses spinal anatomy, spinal physiology, disc degeneration, surgical and non-surgical treatments of disc disease, and the advantages of prosthetic disc replacement.

The annulus is formed of 10 to 60 fibrous bands which serve to control vertebral motion. One half of the bands tighten to check motion when the vertebra above or below the disc are turned in either direction. Restoring disc height returns tension to the annular noted in the prosthetic disc patent application. In addition, restoring annular tension decreases annular protrusion into the spinal canal or neural foramen. Thus, decreasing annular protrusion may eliminate pressure on the spinal cord or nerve roots.

At times the rotational, translational, and axial compression forces exceed the strength of the annular fibers. The excessive forces tear the annular fibers. A single event can tear one band to all the bands. Subsequent tears can connect to previous tears of a few bands resulting in a hole through the entire annulus fibrosis. Holes through the entire annulus fibrosis can result in extrusion of the nucleus pulpous. Extrusion of the nucleus pulpous is referred to as a "herniated disc." Disc herniation can result in back pan, neck pain, arm pain, leg pain, nerve or spinal cord injury, or a combination of the above.

Since the annulus is innervated with pain fibers, acute annular tears without herniation of the nucleus can be painful. Unfortunately, the annular tears often do not heal completely. The chronic tears can result in neck pain, back pain, shoulder pain, buttock pain, or thigh pain. The chronic tears weaken the annulus fibrosis predisposing the disc to herniation or additional annular tears. My U.S. Pat. No. 6,340,369, entitled "Treating Degenerative Disc Disease With Harvested Disc Cells and Analogies of the Extracellular Matrix," and co-pending patent application Ser. No. 09/415,382, entitled "Artificial Intervertebral Disc Replacement Method And Apparatus" describe methods and apparatus for occluding annular defects.

Prosthetic replacement of the nucleus pulpous alone risks future problems arising from annular tears. Patients may continue to complain of pain from the stresses placed onto the weakened annulus. Secondly, tears of the annulus could result in extrusion of the prosthetic nucleus. In addition, remaining nucleus pulpous could herniate through annular tears.

Some prosthetic disc designs attempt to replace nucleus and annular functions. In general, these designs attach the prosthetic disc to the vertebrae. Many of the techniques in this area attach the prosthetic disc to the end plates of the vertebrae with screws, spikes, flanges, or porous surfaces for bone ingrowth. My U.S. Pat. No. 6,245,107 and co-pending patent application Ser. No. 09/415,382 describe methods and devices to assist the annulus in retaining remaining nucleus pulpous and a prosthetic nucleus. The entire contents of these applications are incorporated herein by reference.

The need remains, however, for a more extensive annulus augmentation technique. Failure at the disc vertebra interface could result in loosening of the prosthesis, however, and patients with loose prosthetic discs would likely require revision surgery.

SUMMARY OF THE INVENTION

This invention resides in a device and method for fortifying an intervertebral disc having an annulus fibrosis with an inner wall. According to the method, a hole is formed through the annulus fibrosis, and a collapsed bag is inserted into the disc through the hole. The bag is inflated, or allowed to expand within the disc space, then filling with one or more biocompatible materials. The hole in the annulus fibrosis is then closed. In one preferred embodiment, the bag includes an inflatable bladder or balloon which is filled with a gas or liquid to expand the bag. In an alternative preferred embodiment, the bag includes a self-expanding frame that assumes a collapsed state for introduction into the disc space and an expanded state once inserted through the hole in the annulus. The self-expanding frame is composed of a shape-memory material, for example. The bag preferably features a wall which is porous to allow for the diffusion of body fluids therethrough, and the bag and/or frame may be fastened to the inner wall of the annulus at one or more points.

The biocompatible material may include autograft nucleus pulposis, allograft nucleus pulposis or xenograft nucleus pulposis. In the preferred embodiment, the biocompatible material includes morselized nucleus or annulus from the same disc.

DETAILED DESCRIPTION OF THE INVENTION

This invention broadly resides in annulus augmentation devices, wherein some form of a bag or sac is compressed, inserted into an intervertebral disc space, then expanded or allowed to expand, after which time it is filled with one or more materials or substances conducive to ingrowth or other desirable functions.

Figure 1:
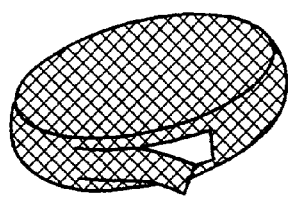
FIG. 1 is a perspective drawing of an annulus augmentation device according to this invention.

FIG. 1 is a simplified drawing from an oblique perspective illustrating an inflatable annulus augmentation device according to the invention. Although a door-like flap is shown, other openings/closings structures may be used, including slits, depending upon the embodiment.

In terms of usage, the device is placed inside the disc to hold material when the flap is closed and secured. For example, the flap may be sewn in a closed position. In the preferred embodiment, the device 100 is porous to allow for the diffusion of body fluids across the walls of the device. As discussed in further detail below, the device may be filled with various materials, including morselized nucleus pulposus from the same disc. For example, nucleus removed in accordance with current procedures may be placed inside the annulus device. The walls of the device the trap the material(s) once inside. The tissue may also be woven or stapled into the mesh bag or frame described below to further deter migration of the contents.

Figure 2A:
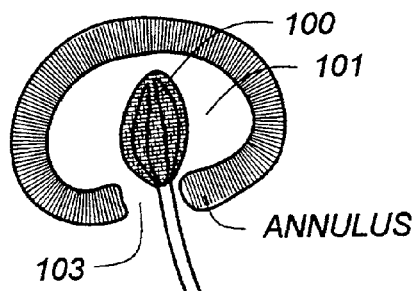
FIG. 2A illustrates the step of inserting the device of FIG. 1 into a disk space.

FIG. 2A begins a series of drawings which show how the embodiment of FIG. 1 is introduced into a disc space 101. In this case, the annulus augmentation device 100 includes a balloon or bladder which is inflated with a syringe 102. The syringe 102 is filled with air though liquids such as water or saline solution may instead be used. The annulus device is such that it may be collapsed for insertion through a hole 103 in the annulus.

Figure 2B:
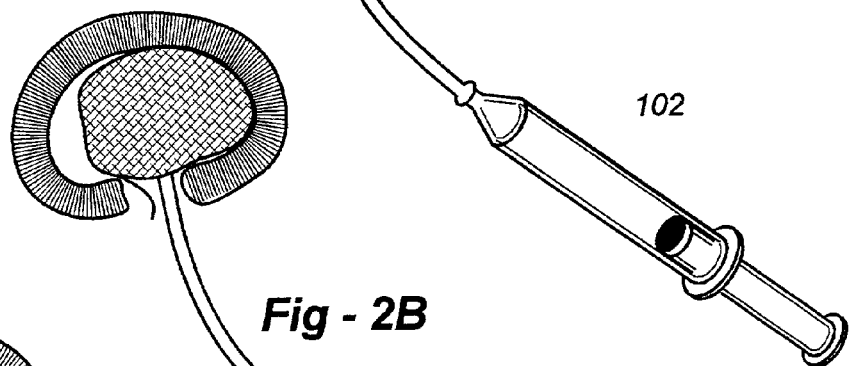
FIG. 2B illustrates the inflation of the device of FIG. 1.
Figure 2C:
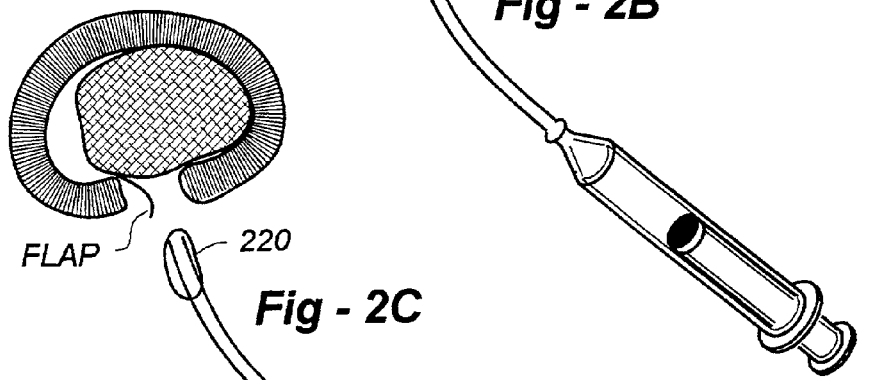
FIG. 2C illustrates the step of removing a deflator and balloon from the device of FIG. 1.
Figure 2C:
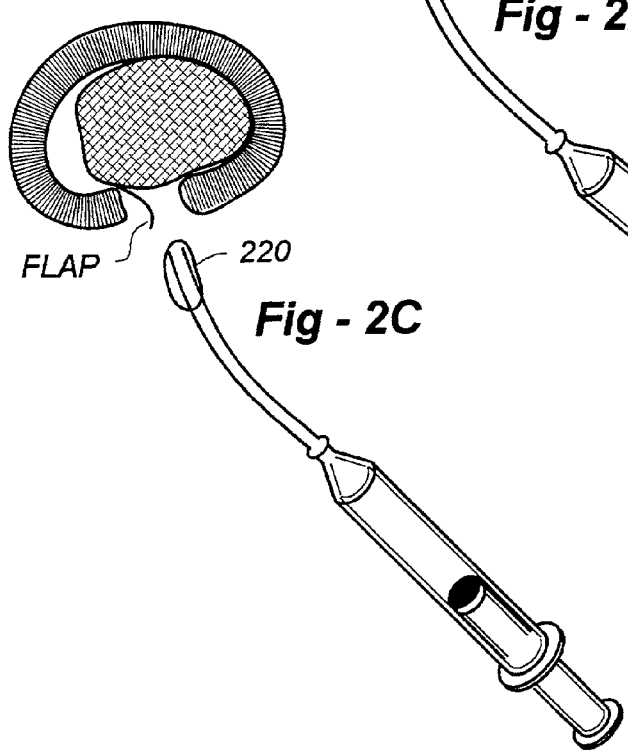
Figure 2D:
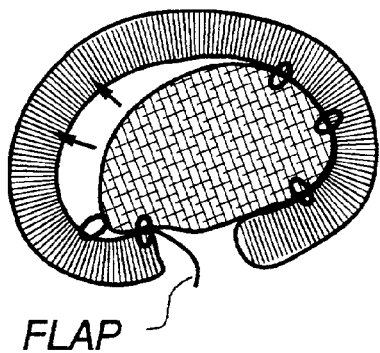
FIG. 2D illustrates the optional insertion of an attachment device.
Figure 2E:
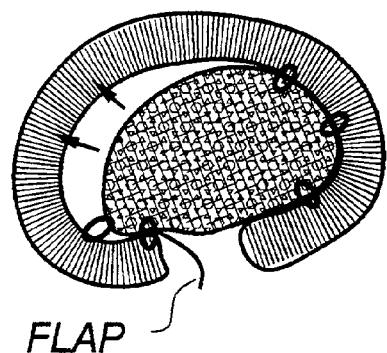
FIG. 2E illustrates the introduction of nucleus pulposus material into the augmentation device.

In FIG. 2B, the balloon is inflated to expand annulus augmentation device, and in FIG. 2C the balloon 220 is deflated and removed. Optional attachment devices such as sutures, staples, and so forth, may be inserted through the annulus augmentation device and into disc tissue, as shown in FIG. 2D. As a further option, autologous nucleus pulposus material may be inserted into the annulus augmentation device, as shown in FIG. 2E.

In the preferred embodiment, morselized nucleus and/or annulus from the same disc is used for this purpose, though other biocompatible materials may alternatively be used. In addition to autograft nucleus pulposus, the device may be filled with allograft nucleus pulposus, xenograft nucleus pulposus, other tissue and/or synthetic materials such hydrogels. Following the introduction of such material(s), the flap or incision is closed and secured.

Figure 3:
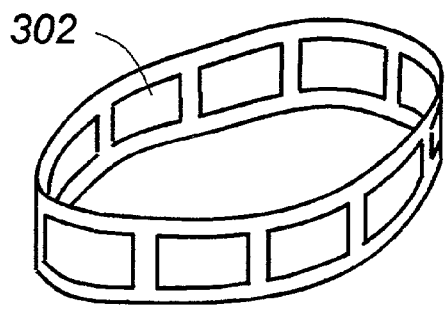
FIG. 3 is an oblique view of a preferred frame structure which may be optionally introduced into the augmentation device of FIG. 1.
Figure 6:
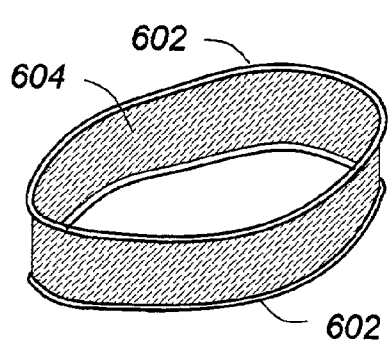
FIG. 6 is a drawing which shows an alternative frame containing two or more spring-like hoops.

As opposed to an active inflation of the bag through external expansion, a self-expanding structure may be used. As shown in FIG. 3, for example, a frame 302 having spring-like properties may be used. As shown in FIG. 6, the frame inside the bag may also contain two or more spring-like hoops 602 separated by an elastic material 604 such as rubber or silicone. The frame, or a portion of the material separating the hoops of the frame, could also be composed of a shape memory material enabling the device to change from a shape with a hole (to allow the bag to be filled) to a shape with a small slit (to close the hole).

Figure 4A:
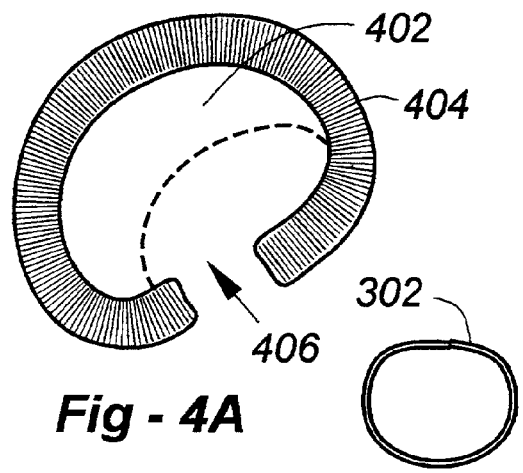
FIG. 4A is a top-view of the frame prior to insertion into a hole in the annulus.
Figure 4B:
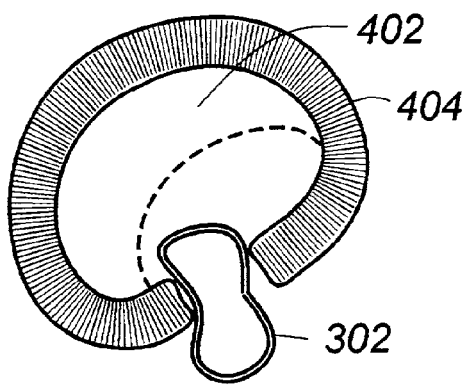
FIG. 4B illustrates the introduction of the frame of FIG. 3 in a collapsed state being inserted into a disc.
Figure 4C:
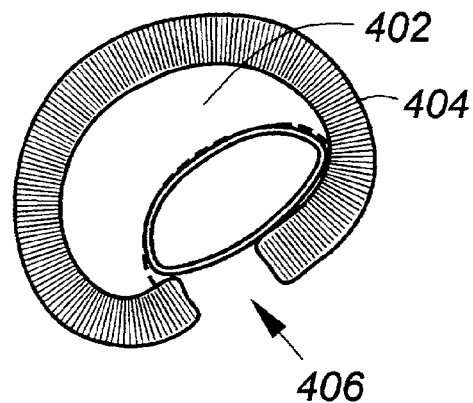
FIG. 4C illustrates the frame expanded within the disc space.
Figure 4D:
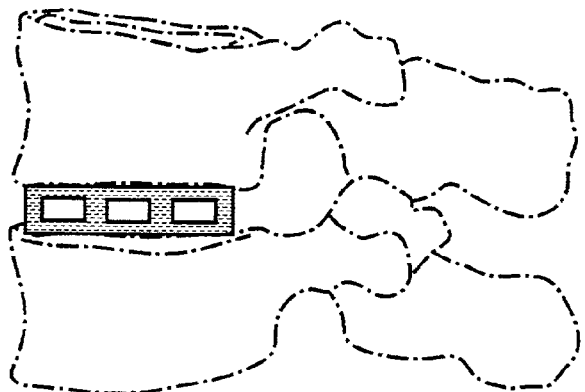
FIG. 4D is a side view of the frame within the disc space prior to any flexion of extension of the spine.
Figure 5:
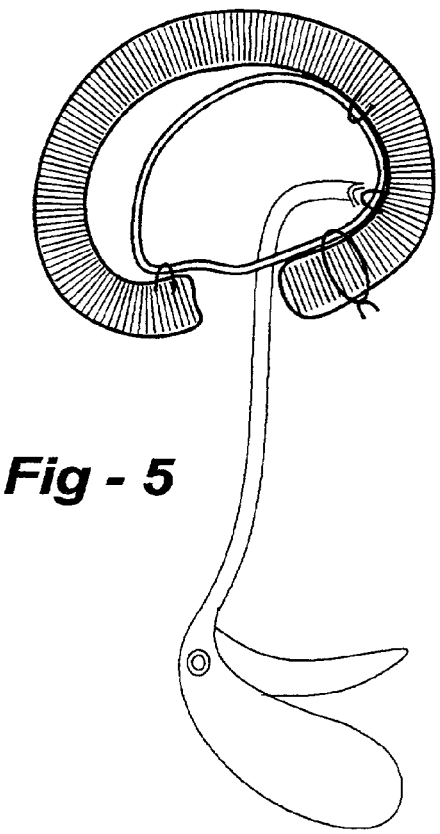
FIG. 5 is a top-down drawing in cross-section showing how the bag may be stapled inside of the disc or, alternatively, sewn to the disc from outside of the disc to stabilize the structure.
Figure 4E:
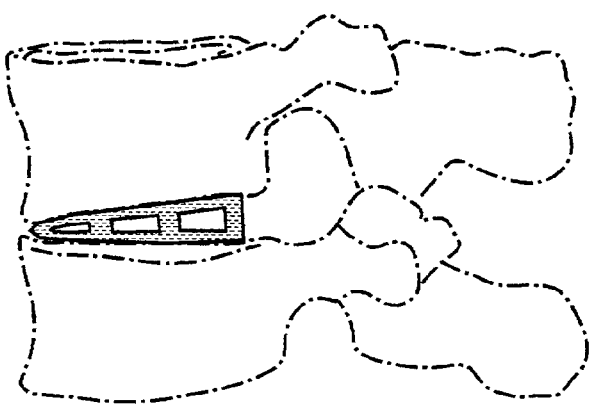
FIG. 4E illustrates flexion of the spine, showing how the frame bends to allow such movement.
Figure 4F:
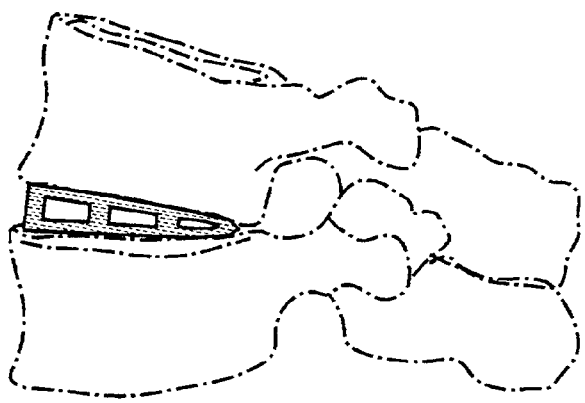
FIG. 4F is a drawing which shows extension of the spine, wherein the back of the frame bends to allow such movement.

FIG. 4A begins a series of drawings used to illustrate how the frame may be inserted (in conjunction with a surrounding bag or sac). FIG. 4A is an axial view of the disc, showing the nucleus pulposus 402, annulus fibrosis 404, and a hole 406 in the annulus. FIG. 4B shows the insertion of collapsed frame and bag into the disc, and FIG. 4C shows the expanded frame within the disc. FIGS. 4D through 4F are side views of the spine, with FIGS. 4E and 4F respectively illustrating how a preferred frame structure accommodates flexion and extension, with the frame returning to a neutral position as the spine returns to neutral position. Note that the back of frame bends to allow extension, and, similarly, the back of the frame returns to neutral position as the spine returns to neutral position.

I claim:

1. An augmentation device for an intervertebral disc having an annulus fibrosis, comprising:
    a bag which is porous to allow for the diffusion of body fluids therethrough;
    a self-expanding frame within the bag; and
    wherein the bag and frame combination exhibits a compression state facilitating introduction into the disc through a hole formed in the annulus, and an expanded state assumed after the bag and frame combination is inserted into the disc.

2. The device of claim 1, wherein the self-expanding frame is composed of a shape-memory material.

3. The device of claim 1, further including a biocompatible material within the bag and frame combination.

4. The device of claim 3, wherein the biocompatible material includes autograft nucleus pulposis, allograft nucleus pulposis or xenograft nucleus pulposis.

5. The device of claim 3, wherein the biocompatible material includes morselized nucleus or annulus from the same disc.

6. The device of claim 1, further including a biologic material within the bag and frame combination.

7. The device of claim 6, wherein the biologic material includes tissues, cells, or extracellular matrix components.

8. A method of fortifying an intervertebral disc having an annulus fibrosis with an inner wall between opposing vertebral endplates, comprising the steps of:
    forming a hole through the annulus fibrosis while preserving the vertebral endplates;

inserting a collapsed bag into the disc through the hole in the annulus fibrosis, the bag including a self-expanding frame that assumes a collapsed state for introduction into the disc space and an expanded state once inserted through the hole in the annulus;

inflating or allowing the bag to expand within the disc space;

filling the expanded bag with one or more biologic or biocompatible materials; and closing the hole in the annulus fibrosis.

9. The method of claim 8, wherein the bag includes an inflatable bladder or balloon which is filled with a gas or liquid to expand the bag.

10. The method of claim 8, wherein the self-expanding frame is composed of a shape-memory material.

11. The method of claim 8, wherein the bag features a wall which is porous to allow for the diffusion of body fluids therethrough.

12. The method of claim 8, further including the step of fastening the bag to the inner wall of the annulus at one or more points.

13. The method of claim 8, further including the step of fastening the frame to the inner wall of the annulus at one or more points.

14. The method of claim 8, wherein the biologic material includes tissues, cells, or extracellular matrix components.

15. The method of claim 8, wherein the biocompatible material includes autograft nucleus pulposis, allograft nucleus pulposis or xenograft nucleus pulposis.

16. The method of claim 8, wherein the biocompatible material includes morselized nucleus or annulus from the same disc.

17. A method of fortifying an intervertebral disc having an annulus fibrosis with an inner wall, comprising the steps of:
forming a hole through the annulus fibrosis;
providing an implant in the form of a covered frame having a collapsed state and an expanded state;
inserting the implant in the collapsed state into the disc through the hole in the annulus fibrosis;
filling the implant with a gas or liquid to expand the covered frame within the disc space;
filling the expanded implant with one or more biologic or biocompatible materials; and
closing the hole in the annulus fibrosis.

18. The method of claim 17, wherein the frame is a self-expanding frame composed of a shape-memory material.

19. The method of claim 17, wherein the covering is porous to allow for the diffusion of body fluids therethrough.

20. The method of claim 17, further including the step of fastening the covering of the frame to the inner wall of the annulus at one or more points.

21. The method of claim 17, further including the step of fastening the frame to the inner wall of the annulus at one or more points.

22. The method of claim 17, wherein the biologic material includes tissues, cells, or extracellular matrix components.

23. The method of claim 17, wherein the biocompatible material includes autograft nucleus pulposis, allograft nucleus pulposis or xenograft nucleus pulposis.

24. The method of claim 17, wherein the biocompatible material includes morselized nucleus or annulus from the same disc.

25. A method of fortifying an intervertebral disc having an annulus fibrosis with an inner wall, comprising the steps of:
forming a hole through the annulus fibrosis;
inserting a collapsed bag into the disc through the hole in the annulus fibrosis;
inflating or allowing the bag to expand within the disc space;
fastening the bag to the inner wall of the annulus fibrosis at one or more points;
filling the expanded bag with one or more biologic or biocompatible materials; and
closing the hole in the annulus fibrosis.

26. The method of claim 25, wherein the bag includes an inflatable bladder or balloon which is filled with a gas or liquid to expand the bag.

27. The method of claim 25, wherein the bag includes a self-expanding frame that assumes a collapsed state for introduction into the disc space and an expanded state once inserted through the hole in the annulus.

28. The method of claim 27, wherein the self-expanding frame is composed of a shape-memory material.

29. The method of claim 25, wherein the bag features a wall which is porous to allow for the diffusion of body fluids therethrough.

30. The method of claim 27, further including the step of fastening the frame to the inner wall of the annulus at one or more points.

31. The method of claim 25, wherein the biologic material includes tissues, cells, or extracellular matrix components.

32. The method of claim 25, wherein the biocompatible material includes autograft nucleus pulposis, allograft nucleus pulposis or xenograft nucleus pulposis.

33. The method of claim 25, wherein the biocompatible material includes morselized nucleus or annulus from the same disc.

34. A method of fortifying an intervertebral disc having an annulus fibrosis with an inner wall, comprising the steps of:
forming a hole through the annulus fibrosis;
inserting a collapsed bag into the disc through the hole in the annulus fibrosis, including a self-expanding frame that assumes a collapsed state for introduction into the disc space and an expanded state once inserted through the hole in the annulus;
inflating or allowing the bag to expand within the disc space;
filling the expanded bag with disc tissue or tissues that function like disc tissue; and
closing the hole in the annulus fibrosis.

35. The method of claim 34, wherein the bag includes an inflatable bladder or balloon which is filled with a gas or liquid to expand the bag.

36. The method of claim 34, wherein the bag includes a self-expanding frame that assumes a collapsed state for introduction into the disc space and an expanded state once inserted through the hole in the annulus.

37. The method of claim 34, wherein the self-expanding frame is composed of a shape-memory material.

38. The method of claim 34, wherein the bag features a wall which is porous to allow for the diffusion of body fluids therethrough.

39. The method of claim 34, further including the step of fastening the bag to the inner wall of the annulus at one or more points.

40. The method of claim 34, further including the step of fastening the frame to the inner wall of the annulus at one or more points.

41. The method of claim 34, wherein the tissue includes disc cells or extracellular matrix components.

42. The method of claim 34, wherein the tissue includes autograft nucleus pulposis, allograft nucleus pulposis or xenograft nucleus pulposis.

43. The method of claim 34, wherein the tissue includes morselized nucleus or annulus from the same disc.

44. A method of fortifying an intervertebral disc having an annulus fibrosis with an inner wall, comprising the steps of:
  forming a hole through the annulus fibrosis;
  inserting a collapsed bag into the disc through the hole in the annulus fibrosis;
  inflating or allowing the bag to expand within the disc space;
  filling the expanded bag with disc tissue or tissues that function like disc tissue; and
  fastening the bag to the inner wall of the annulus at one or more points;
  closing the hole in the annulus fibrosis.

45. A method of fortifying an intervertebral disc having an annulus fibrosis with an inner wall, comprising the steps of:
  forming a hole through the annulus fibrosis;
  providing an implant in the form of a covered frame having a collapsed state and an expanded state;
  inserting the implant in the collapsed state into the disc through the hole in the annulus fibrosis;
  inflating or allowing the covered frame to expand within the disc space;
  filling the expanded implant with one or more biologic or biocompatible materials; and
  fastening the frame to the inner wall of the annulus at one or more points;
  closing the hole in the annulus fibrosis.

46. A method of fortifying an intervertebral disc having an annulus fibrosis with an inner wall, comprising the steps of:
  forming a hole through the annulus fibrosis;
  providing an implant in the form of a covered frame having a collapsed state and an expanded state;
  inserting the implant in the collapsed state into the disc through the hole in the annulus fibrosis;
  inflating or allowing the covered frame to expand within the disc space;
  filling the expanded implant with one or more biologic or biocompatible materials including includes autograft nucleus pulposis, allograft nucleus pulposis or xenograft nucleus pulposis; and
  closing the hole in the annulus fibrosis.

47. A method of fortifying an intervertebral disc having an annulus fibrosis with an inner wall, comprising the steps of:
  forming a hole through the annulus fibrosis;
  providing an implant in the form of a covered frame having a collapsed state and an expanded state;
  inserting the implant in the collapsed state into the disc through the hole in the annulus fibrosis;
  inflating or allowing the covered frame to expand within the disc space;
  filling the expanded implant with one or more biologic or biocompatible materials including morselized nucleus or annulus from the same disc; and
  closing the hole in the annulus fibrosis.

* * * * *